United States Patent [19]

Weilbacher

[11] Patent Number: 4,465,483
[45] Date of Patent: Aug. 14, 1984

[54] MODULAR DRAINAGE APPARATUS

[75] Inventor: Eugene E. Weilbacher, New Philadelphia, Ohio

[73] Assignee: Snyder Laboratories, Inc., Dover, Ohio

[21] Appl. No.: 386,242

[22] Filed: Jun. 8, 1982

[51] Int. Cl.³ .............................................. A61M 1/00
[52] U.S. Cl. ..................................... 604/317; 137/205
[58] Field of Search ................ 137/205; 604/317, 318, 604/323, 324, 319–321; 128/760, 767

[56] References Cited

U.S. PATENT DOCUMENTS

| 3,783,870 | 1/1974 | Schachet | 604/321 |
| 4,018,224 | 4/1977 | Kurtz et al. | 604/321 |
| 4,195,633 | 4/1980 | Nehring et al. | 604/320 |
| 4,289,158 | 9/1981 | Nehring | 137/205 |

Primary Examiner—C. Fred Rosenbaum
Assistant Examiner—J. L. Kruter
Attorney, Agent, or Firm—Frank C. Leach, Jr.

[57] ABSTRACT

A modular drainage apparatus has a plurality of preformed plastic bodies supported by a header. One of the bodies includes a collection chamber connected to the pleural cavity of a patient and connected to a first passage formed in the header. A second body includes a U-shaped liquid seal chamber having one end connected to the first passage and its other end connected to a second passage formed in the header. The second passage is connected to a vacuum pump, which creates a suction within the collection chamber through the liquid seal chamber. A third body includes a U-shaped chamber to regulate the negative pressure produced by the vacuum pump to a desired negative pressure. The second body also includes a second U-shaped chamber having one end connected to the atmosphere and its other end connected to the liquid seal chamber adjacent its connection to the first passage. By filling each leg of the second U-shaped chamber of the second body to a selected level with a liquid, the negative pressure in the collection chamber is maintained at a selected maximum above the pressure maintained in the collection chamber by the vacuum pump and regulated by the U-shaped chamber of the third body.

23 Claims, 19 Drawing Figures

MODULAR DRAINAGE APPARATUS

This invention relates to a modular apparatus for supporting bodies from support means and, more particularly, to a modular drainage apparatus for supporting bodies from support means including one body receiving fluids drained from a pleural cavity of a body.

Various types of drainage apparatuses have been developed for use in draining fluids from the pleural cavity of a human being in a clean and aseptic environment. Examples of these drainage apparatuses are disclosed in U.S. Pat. No. 3,363,626 to Bidwell et al, U.S. Pat. No. 3,363,627 to Bidwell et al, U.S. Pat. No. 3,559,647 to Bidwell et al, U.S. Pat. No. 3,683,913 to Kurtz et al, U.S. Pat. No. 3,757,783 to Alley, U.S. Pat. No. 3,783,870 to Schachet, U.S. Pat. No. 3,853,128 to Kurtz et al, U.S. Pat. No. 3,924,624 to Schachet, U.S. Pat. No. 3,946,735 to DeWall, U.S. Pat. No. 4,195,633 to Nehring et al, and U.S. Pat. No. 4,289,158 to Nehring.

In the aforesaid U.S. Pat. No. 3,924,624 to Schachet, there is shown a modular device for thoracic drainage. However, this device has each of the chambers, which are separate bodies, connected solely to each other and requires a specific type of structural connection between the chambers. The structure of the aforesaid U.S. Pat. No. 3,924,624 to Schachet relies upon plastic tubing to provide the air communicating connections between the chambers. The plastic tubing has the possibility of ceasing to maintain the desired seal between the chambers so that the aseptic evironment may be lost with the modular device of the aforesaid U.S. Pat. No. 3,924,624 to Schachet.

The modular apparatus of the present invention overcomes the foregoing problem of the device of the aforesaid U.S. Pat. No. 3,924,624 to Schachet in that the aseptic environment cannot be lost. This is accomplished through providing common support means for each of the separate plastic bodies with each body being disposed at a specific location on the support means. This insures that there is a common connecting means between the various bodies rather than having the bodies connected to each other directly for their sole connections. This avoids any necessity of plastic tubings as the air communication connection means. Additionally, seals, which are used instead of the plastic tubing, are located so that they cannot be readily tampered with; thus, this avoids the possible loss of the aseptic environment.

In the aforesaid U.S. Pat. No. 3,924,624 to Schachet, the adjacent chambers of the modular device are secured to each other by pins extending through tabs or extensions at both the upper and lower ends of the adjacent chambers. This is a time consuming assembly. This also requires each of the chambers to be supported by the adjacent chamber or chambers.

In the modular apparatus of the present invention, all of the separate bodies are supported from the common or single support means, which has means providing air communication between the various chambers as desired. Thus, there is no necessity to utilize any type of pin construction for securing the bodies to each other.

In the apparatus of the present invention, the lower ends of the bodies are releasably connected to each other to provide a more stable and compact device. However, such is not a requisite to form the modular apparatus of the present invention since all of the bodies are supported by the single support means.

Furthermore, by using the single support means, precise positioning of each of the bodies relative to each other and to the single support means is easily obtained. This insures that each of the bodies is properly disposed relative to the chamber comunicating means with which it communicates.

In the aforesaid U.S. Pat. No. 3,924,624 to Schachet, it would be difficult to replace the collection chamber if it becomes filled. With the modular apparatus of the present invention, the body having the collection chamber can be easily replaced if the collection chamber becomes filled.

An object of this invention is to provide a modular apparatus.

Another object of this invention is to provide a modular apparatus for supporting a plurality of bodies having chambers selectively communicating with each other.

Other objects of this invention will be readily perceived from the following description, claims, and drawings.

This invention relates to a modular apparatus including a plurality of bodies with each body including at least one chamber having an upper wall and each of the bodies having a groove on each side thereof adjacent at least the upper wall of the one chamber. The modular apparatus has support means to support each of the bodies with the support means having a longitudinally extending wall and means for disposition within the grooves in each of the bodies to cause each of the bodies to have the upper wall of at least the one chamber abut the longitudinally extending wall of the support means.

The attached drawings illustrate a preferred embodiment of the invention, in which.

Figures 1, 1A:
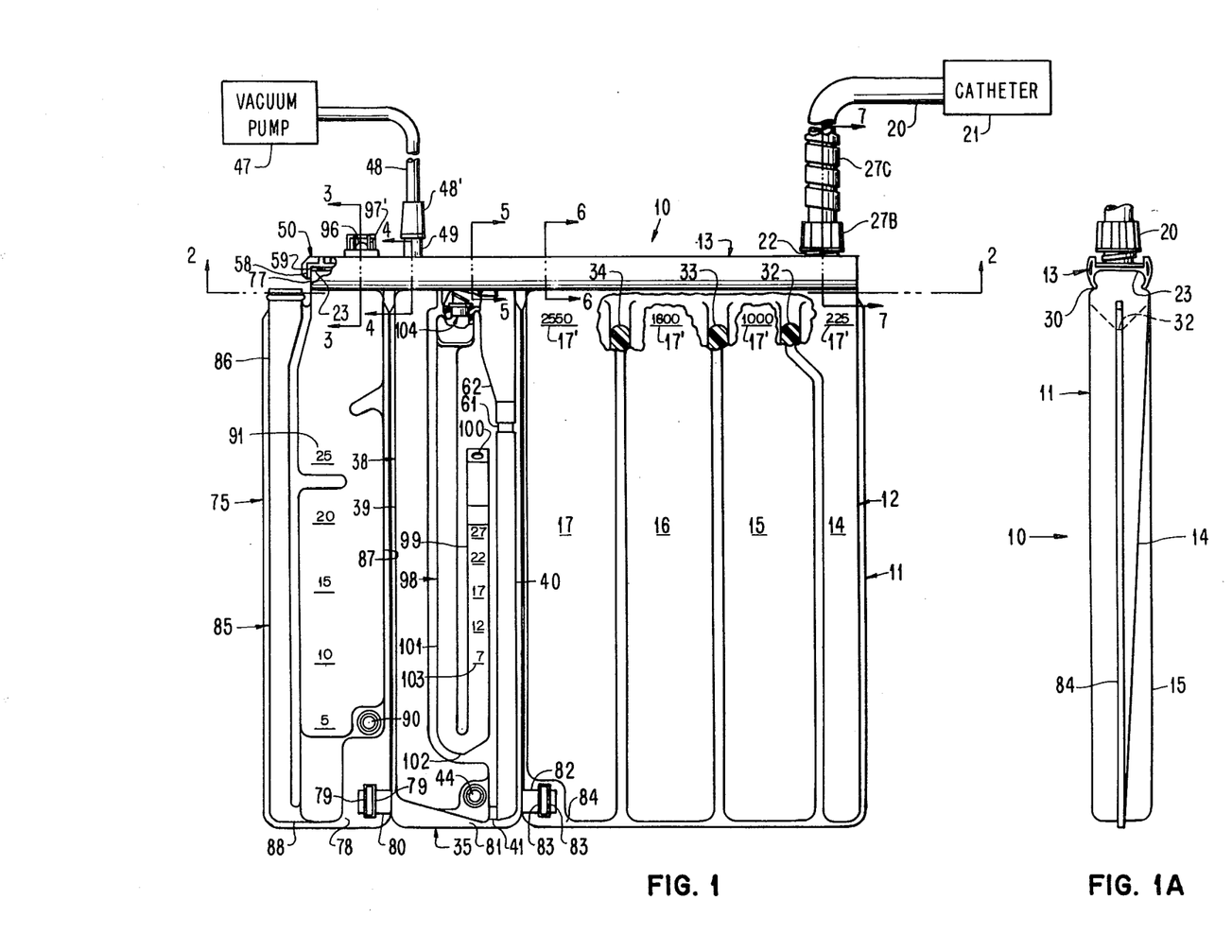
FIG. 1 is a front elevational view, partly schematic, of the modular apparatus of the present invention.
FIG. 1A is an end elevational view of the modular apparatus of FIG. 1.

Referring to the drawings and particularly FIG. 1, there is shown a drainage apparatus 10 for draining fluid from the pleural cavity of a patient. The drainage apparatus 10 is a modular configuration.

The drainage apparatus 10 includes a first transparent plastic body or unit 11 having a collection or trap chamber 12 for receiving fluids from the pleural cavity of the patient. The first body or unit 11 is supported by a header 13, which functions as support means for the body or unit 11, and is preferably a non-transparent plastic.

The collection chamber 12 is divided into four compartments 14, 15, 16, and 17. The compartment 14 is much smaller than each of the compartments 15, 16, and 17 so that it may be used as a special pediatric compartment to measure the quantity of the liquids in the fluids obtained from the pleural cavity of a child when the drainage apparatus 10 is used with a child.

The compartment 14 holds 225 cc of liquids. The compartment 15 retains 775 cc of liquids. The compartment 16 holds 800 cc of liquids, and the compartment 17 retains 750 cc of liquids. Thus, the compartments 14-17 can hold a total volume of 2550 cc of liquids. Each of the compartments 14-17 has indicia 17' to indicate the total volume of liquids collected in the collection chamber 12.

The collection chamber 12 has an inlet 18 (see FIG. 7) in its substantially horizontal upper wall 19 above the compartment 14, which is the pediatric compartment. Thus, the liquids from the fluids obtained from the pleural cavity of any patient connected to the drainage apparatus 10 are initially collected in the compartment 14.

The inlet 18 of the collection chamber 12 communicates with the pleural cavity of a patient through a flexible tube 20 (see FIG. 1). The tube 20 has one end connected to the pleural cavity of the patient through a catheter 21, for example, and its other end extending into a hollow fitting 22, which is fixed to the upper surface of a horizontally extending wall 23 (see FIG. 7) of the header 13 and has threads on its outer surface.

Figure 7:
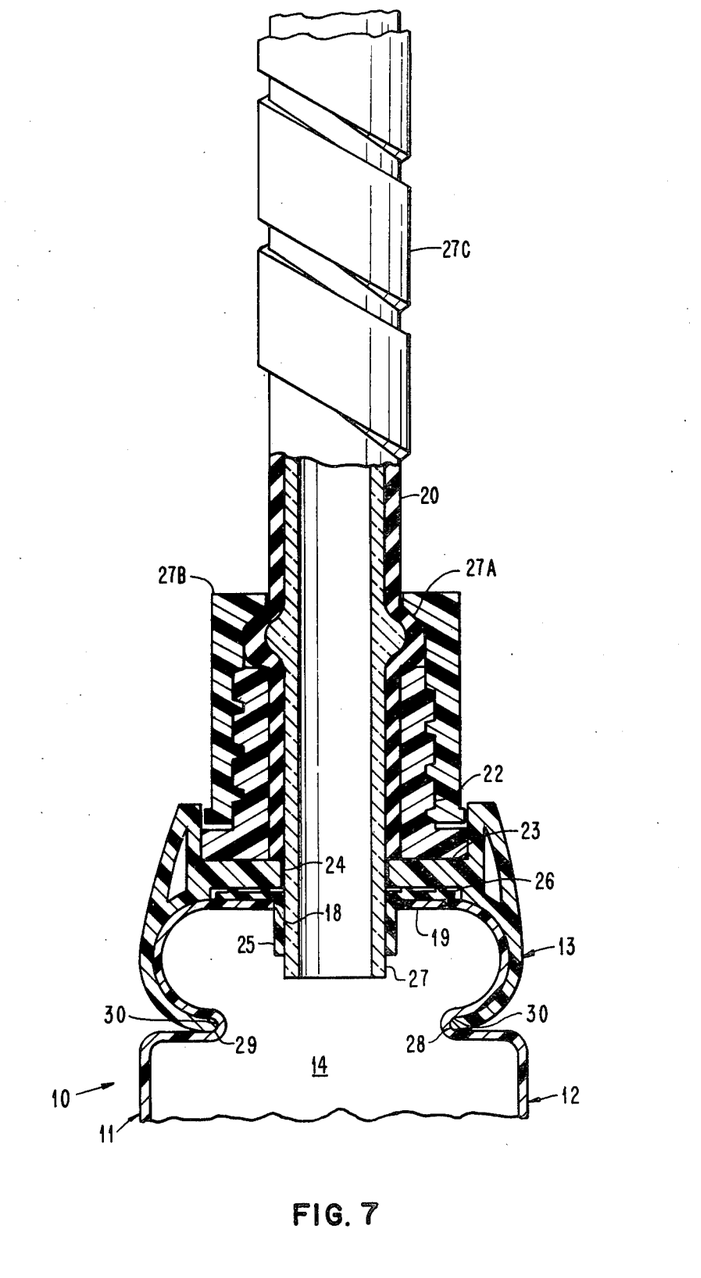
FIG. 7 is a fragmentary sectional view of the modular apparatus of FIG. 1 taken along line 7—7 of FIG. 1 and showing the collection chamber communicating with a hose leading to the pleural cavity of a patient.

The horizontally extending wall 23, which extends for the length of the header 13, has a circular passage 24 extending therethrough and communicating with the inlet 18 in the upper wall 19 of the collection chamber 12. A gasket 25, which is formed of a suitable elastomeric material such as nitrile rubber, for example, is disposed within the inlet 18 and has an annular flange 26 abutting against the bottom surface of the wall 23 of the header 13 and surrounding the bottom end of the passage 24 in the wall 23 of the header 13 so as to form a seal therewith whereby the fluids from the pleural cavity of the patient will flow into the compartment 14 of the collection chamber 12.

The flexible tube 20 has a translucent plastic tube 27 disposed in its lower end and extending through the passage 24 in the wall 23 of the header 13 and the interior of the gasket 25 to communicate with the interior of the compartment 14. The extension of the tube 27 into the compartment 14 is controlled by a projection 27A on the flexible tube 20 abutting the upper surface of the fitting 22.

A threaded cap 27B, which has threads on its inner surface cooperating with the threads on the outer surface of the fitting 22, pushes the projection 27A into engagement with the upper surface of the fitting 22 to retain the flexible tube 20 within the hollow fitting 22. This also produces a seal to prevent any leakage of air into the compartment 14.

The outer surface of the portion of the tube 20 adjacent the upper end of the tube 27 has an element 27C, which is formed of a suitable translucent plastic, wrapped therearound and fitting firmly so as to not be mobile. The element 27C prevents any kinking of the flexible tube 20.

The header 13 has its support edges 28 and 29 disposed within slots or grooves 30 formed in the exterior of the upper end of the body 11 on opposite sides thereof to enable the header 13 to support the body 11. Thus, the annular flange 26 of the gasket 25 is held against the bottom surface of the horizontally extending wall 23 of the header 13 to form the seal between the passage 24 in the wall 23 and the inlet 18 in the upper wall 19 of the body 11.

As shown in FIG. 1, the upper end of the compartment 14 of the collection chamber 12 communicates with the upper end of the compartment 15 of the collection chamber 12 by a V-shaped channel or passage 32. Thus, when the compartment 14 becomes filled with liquids so that the compartment 14 has 225 cc of liquids therein, the liquids flow into the compartment 15 through the channel or passage 32.

The upper end of the compartment 15 of the collection chamber 12 communicates through a V-shaped channel or passage 33 with the upper end of the compartment 16. Accordingly, when the compartments 14 and 15 become filled with liquids so that the compartments 14 and 15 have a total of 1000 cc of liquids therein, the liquids enter the compartment 16 through the channel or passage 33.

The upper end of the compartment 16 of the collection chamber 12 communicates with the upper end of the compartment 17 of the collection chamber 12 through a V-shaped channel or passage 34. Therefore, when the compartment 16 becomes filled with liquids so that the compartments 14, 15, and 16 have a total of 1800 cc of liquids therein, the liquids flow into the compartment 17 through the channel or passage 34.

The header 13 supports a second body or unit 35 adjacent the first body 11. The second body 35 has a pair of slots or grooves 36 (see FIG. 5) formed in its exterior on opposite sides thereof adjacent its upper end to receive the edges 28 and 29 of the header 13.

Figure 14:
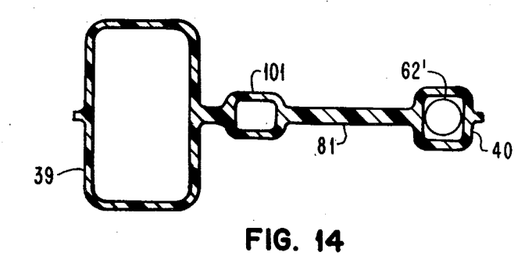
FIG. 14 is a sectional view of the body of FIG. 8 and taken along line 14—14 of FIG. 8.
Figure 15:
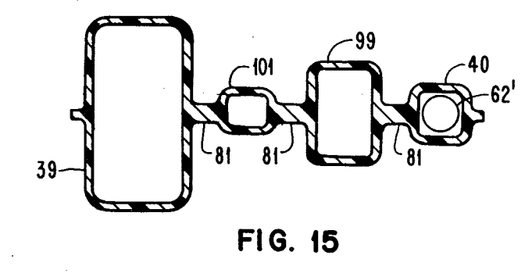
FIG. 15 is a sectional view of the body of FIG. 8 and taken along line 15—15 of FIG. 8.
Figure 16:
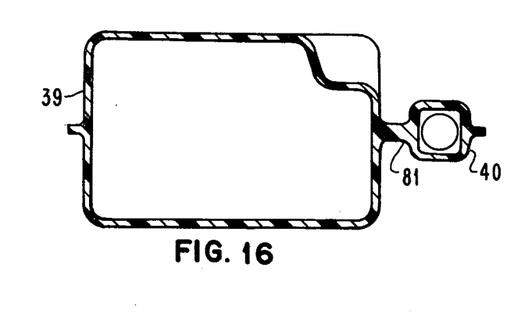
FIG. 16 is a sectional view of the body of FIG. 8 and taken along line 16—16 of FIG. 8.

The body 35 (see FIGS. 1 and 8) includes a liquid seal chamber 38. The liquid seal chamber 38 includes a first column 39 and a second column 40. The relationships of the cross sectional areas of the columns 39 and 40 are shown in FIGS. 14 to 16.

Figure 8:
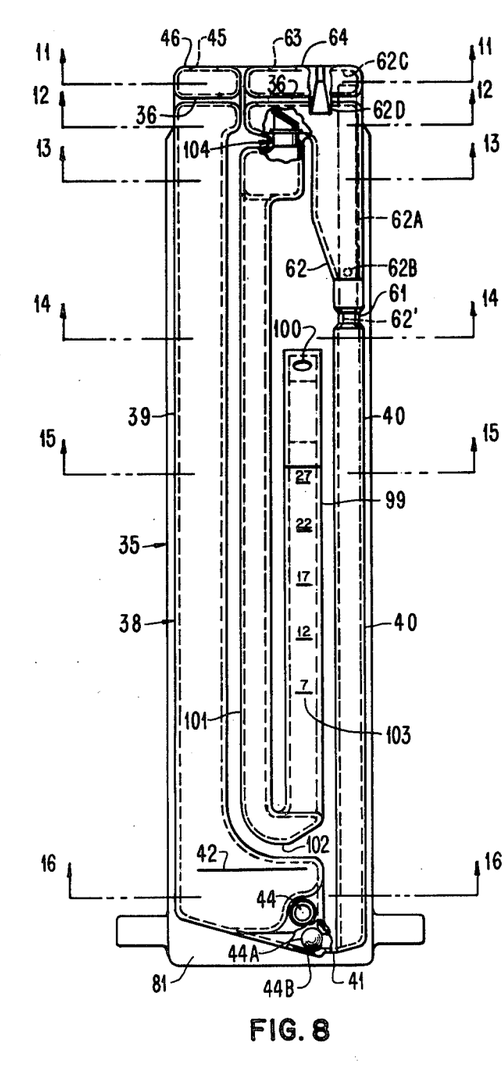
FIG. 8 is a front elevational view, partly in section, of one of the three bodies forming the modular apparatus and including the arrangement for preventing excess negative pressure within the pleural cavity of a patient connected to the modular apparatus.
Figure 9:
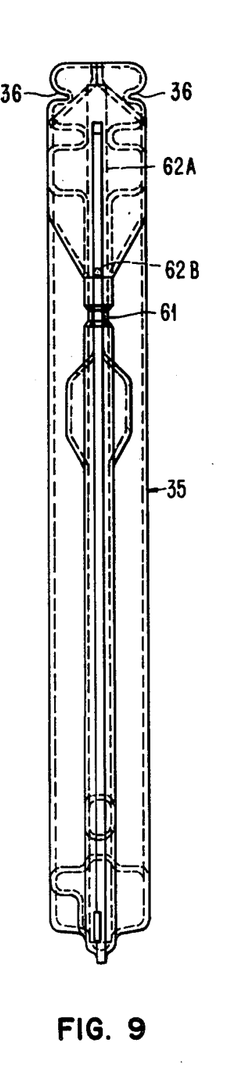
FIG. 9 is an end elevational view of the body of FIG. 8.

The columns 39 and 40 communicate with each other at their bottom ends through a passage 41 so that the liquid seal chamber 38 is substantially U-shaped. Liquid such as water, for example, spans the bottom of the two columns 39 and 40 and extends to a level line 42 as shown in FIG. 8. The liquid such as water, for example, is added to the columns 39 and 40 through a Luer valve 44 (see FIG. 1) in a wall of the liquid seal chamber 38 by adding water to the level line 42 (see FIG. 8).

A ball valve 44A is disposed in the lowermost portion of the first column 39 for cooperation with a valve seat 44B formed by the end of the passage 41 communicating with the bottom of the first column 39. The ball valve 44A does not completely prevent flow of liquid from the first column 39 to the second column 40 but retards flow so that there is no sudden evacuation of the liquid from the liquid seal chamber 38 to the collection chamber 12 (see FIG. 1). The ball valve 44A (see FIG. 8) also prevents large bubbles from flowing to the second column 40 to reduce the possibility of liquid flowing therewith.

Figure 2:
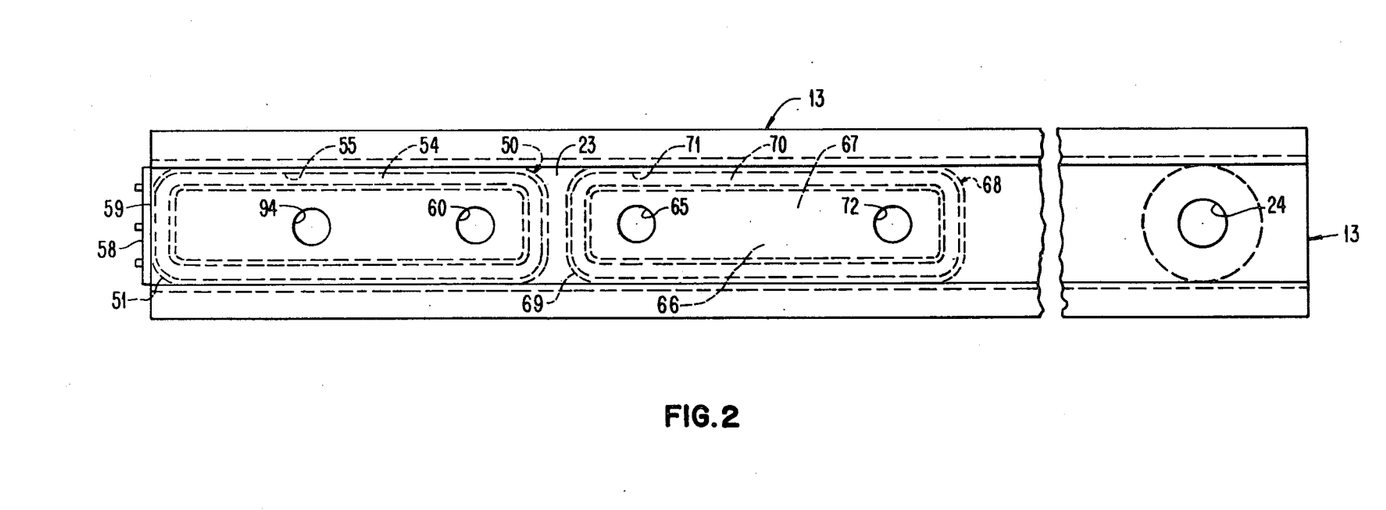
FIG. 2 is a bottom plan view of a header of the modular apparatus of FIG. 1 and taken along line 2—2 of FIG. 1.
Figure 4:
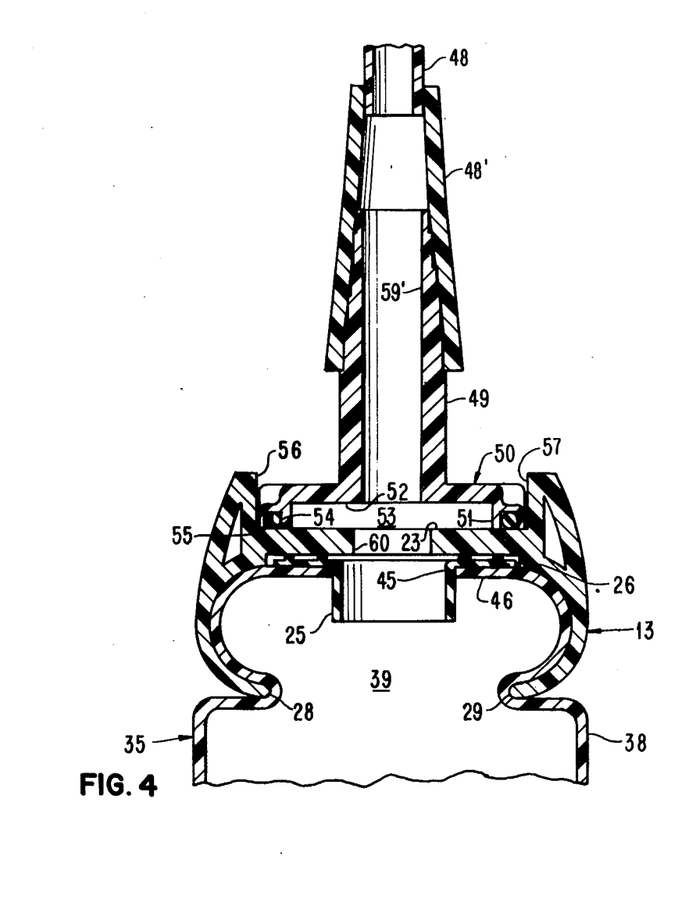
FIG. 4 is a fragmentary sectional view of the modular apparatus of FIG. 1 taken along line 4—4 of FIG. 1 and showing the vacuum pump and the liquid seal chamber communicating with the same sealed chamber.
Figure 10:
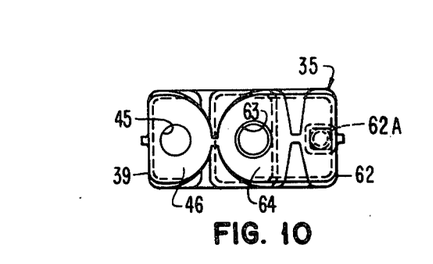
FIG. 10 is a top plan view of the body of FIG. 8.
Figure 11:
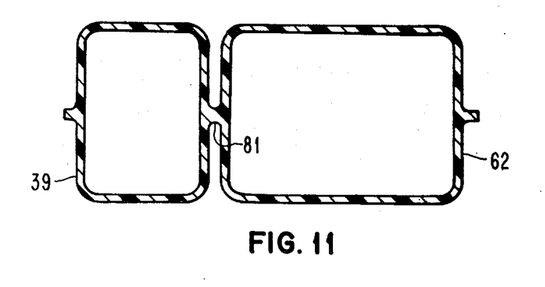
FIG. 11 is a sectional view of the body of FIG. 8 and taken along line 11—11 of FIG. 8.
Figure 12:
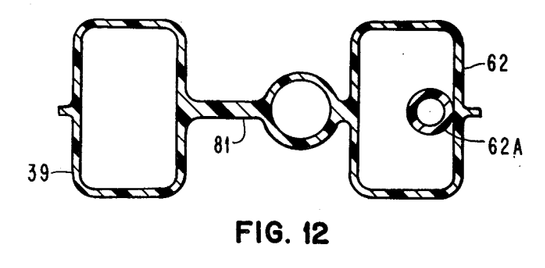
FIG. 12 is a sectional view of the body of FIG. 8 and taken along line 12—12 of FIG. 8.
Figure 13:
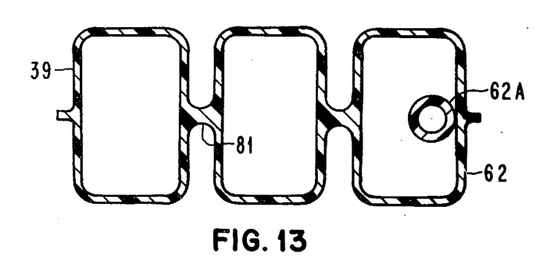
FIG. 13 is a sectional view of the body of FIG. 8 and taken along line 13—13 of FIG. 8.

The first column 39 of the liquid seal chamber 38 has a circular inlet 45 (see FIG. 10) formed in its upper wall 46 for communication with a negative pressure source such as a vacuum pump 47 (see FIG. 1), for example, by a tube 48. The tube 48 is connected by a fitting 48' to a tapered and stepped hollow connector 49, which is formed integral with a manifold plate 50 (see FIGS. 2 and 4).

The manifold plate 50 is supported on the upper surface of the wall 23 of the header 13 and is fixed thereto by any suitable adhesive or bonding means. The manifold plate 50 has a peripheral projection 51 (see FIG. 4) extending downwardly to space a horizontally extending wall 52 of the manifold plate 50 from the upper surface of the wall 23 of the header 13 to form a chamber 53 therebetween. A sealing ring 54 is supported in a peripheral groove 55 in the peripheral projection 51 of the manifold plate 50 to form a seal with the upper surface of the wall 23 of the header 13.

The position of the manifold plate 50 on the header 13 is controlled by disposing the manifold plate 50 between a pair of upstanding walls 56 and 57 of the header 13. The longitudinal position of the manifold plate 50 is controlled by a flange 58 (see FIGS. 1 and 2) on one end of the manifold plate 50 bearing against an end 59 (see FIG. 2) of the wall 23.

As a result, the hollow connector 49 (see FIG. 4) has its passage 59' aligned with a circular passage 60 extending through the wall 23 of the header 13. The passage 60 communicates with the inlet 45 in the upper wall 46 of the first column 39 of the liquid seal chamber 38. The inlet 45 has one of the gaskets 25 disposed therein to form a seal with the passage 60 in the wall 23 of the header 13. Accordingly, the vacuum pump 47 (see FIG. 1) exerts a negative pressure within the chamber 53 (see FIG. 4) and the first column 39 (see FIGS. 1 and 8) of the liquid seal chamber 38.

The second column 40 of the liquid seal chamber 38 has its upper end 61 terminating in the lower end of a reservoir 62 through a reduced circular opening 62' (see FIG. 8) to reduce the rate of liquid escaping therethrough. The reservoir 62 has a vertically disposed bypass tube 62A extending upwardly therein from the reduced circular opening 62'. The tube 62A has holes 62B adjacent its lower end and is open at its upper end to provide communication from the interior of the tube 62A to the interior of the reservoir 62.

This structure prevents loss of any of the liquid from the liquid seal chamber 38 through the reservoir 62 to the collection chamber 12 (see FIG. 1), which is in communication with the reservoir 62 as will be explained hereinafter, when a patient gasps strongly. If a sufficient quantity of the liquid in the liquid seal chamber 38 were removed therefrom by the patient gasping strongly, atmospheric pressure could enter the pleural cavity of the patient if the vacuum pump 47 were disconnected.

When a patient gasps strongly to create a relatively high negative pressure within the patient's pleural cavity, liquid is initially rapidly drawn up the second column 40 (see FIG. 8) of the liquid seal chamber 38 and into the reservoir 62 through the holes 62B and the open upper end of the tube 62A. This rapid and sufficiently higher negativity within the pleural cavity of the patient transfers the liquid in the liquid seal chamber 38 into the reservoir 62.

However, the open upper end of the tube 62A is not blocked by the liquid sucked into the reservoir 62. As a result, air and liquid can flow through the open upper end of the tube 62A into the reservoir 62 for transmittal of air through the collection chamber 12 (see FIG. 1) to the pleural cavity of the patient. When the flow of air up the tube 62A (see FIG. 8) ceases, the liquid in the reservoir 62 immediately drains therefrom through the holes 62B in the tube 62A and down the second column 40 of the liquid seal chamber 38 to again establish the liquid seal in the liquid seal chamber 38. Thus, no liquid is lost from the liquid seal chamber 38.

It should be understood that liquid also passes through the open upper end of the tube 62A and engages a substantially horizontal wall 62C of the reservoir 62. This liquid is retained within the reservoir 62 by a substantially vertical wall 62D so that none of the liquid can escape through an opening 63 (see FIG. 10) in upper wall 64 of the reservoir 62.

The opening 63 communicates with a circular passage 65 (see FIG. 5) extending through the wall 23 of the header 13. The opening 63 has one of the gaskets 25 disposed therein to form a seal between the opening 63 and the passage 65.

Figure 5:
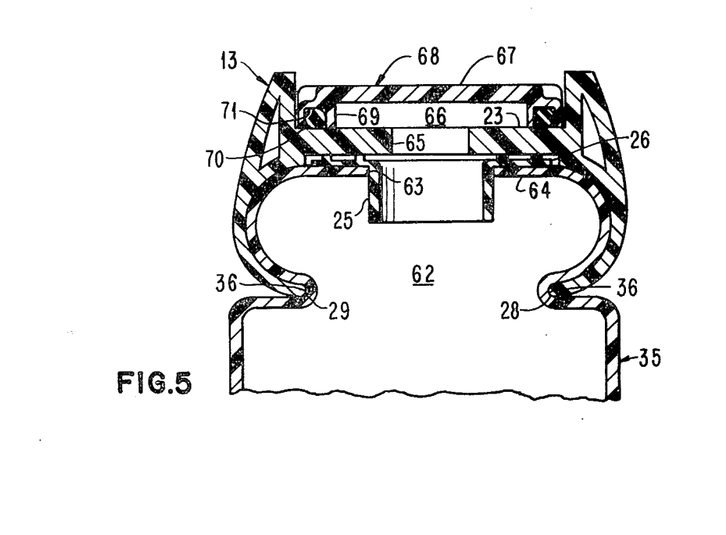
FIG. 5 is a fragmentary sectional view of the modular apparatus of FIG. 1 taken along line 5—5 of FIG. 1 and showing the liquid seal chamber communicating with a second sealed chamber.

The passage 65 in the wall 23 of the header 13 communicates with a chamber 66, which is formed between the wall 23 and a horizontally extending wall 67 of a manifold plate 68. The manifold plate 68 is secured to the wall 23 in the same manner as the manifold plate 50.

Figure 6:
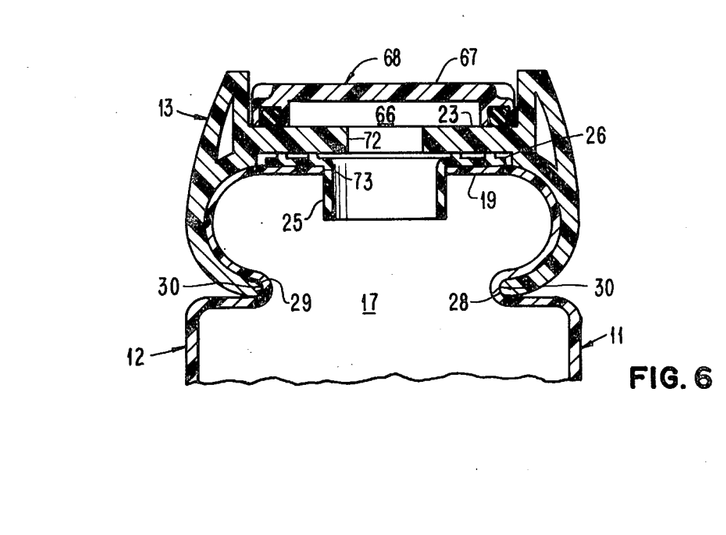
FIG. 6 is a fragmentary sectional view of the modular apparatus of FIG. 1 taken along line 6—6 of FIG. 1 and showing the collection chamber communicating with the second sealed chamber.

The manifold plate 68 has a peripheral projection 69 bearing against the upper surface of the wall 23 to space the wall 67 of the manifold plate therefrom. The peripheral projection 69 has a sealing ring 70 mounted in a peripheral groove 71 in the peripheral projection 69 to seal the chamber 66. The manifold plate 68 is longitudinally positioned on the upper surface of the wall 23 of the header 13 so that the sealed chamber 66 also communicates with a circular passage 72 (see FIG. 6) extending through the wall 23. Thus, the passages 65 (see FIG. 5) and 72 (see FIG. 6) communicate with each other through the sealed chamber 66 so that the sealed chamber 66 functions as passage or communicating means.

The passage 72 is aligned with a circular outlet opening 73 in the upper wall 19 of the collection chamber 12. The outlet opening 73 has one of the gaskets 25 mounted therein to form a seal between the outlet opening 73 and the passage 72. Therefore, the reservoir 62 (see FIG. 1) communicates with the collection chamber 12 above the compartment 17 via the sealed chamber 66 (see FIG. 6).

Thus, the second column 40 (see FIG. 1) of the liquid seal chamber 38 is in communication with the collection chamber 12. Accordingly, any vacuum produced in the liquid seal chamber 38 by the vacuum pump 47 and regulated in a manner to be hereinafter described is created in the collection chamber 12 so that this same negative pressure exists within the pleural cavity of the patient connected to the collection chamber 12 of the drainage apparatus 10 by the tube 20.

A third body or unit 75 also is supported on the header 13. The body 75 has slots or grooves 76 (see FIG. 3) adjacent its upper end on its exterior to receive the edges 28 and 29 of the header 13. The body 75 has an end portion 77 (see FIG. 1) abutting the flange 58 of the manifold plate 50 (see FIG. 2), which is fixed to the header 13, to position the body 75 (see FIG. 1) on the header 13.

The third body 75 has a small portion of the lower end of its common connecting wall 78 punched or pushed out to form a pair of slots 79 to receive a tab 80 integrally formed on the lower end of a common connecting wall 81 of the second body 35. The reception of the tab 80 in the slots 79 joins the bodies 35 and 75 to each other at their lower ends with the adjacent edges of the walls 78 and 81 abutting.

The common connecting wall 81 of the second body 35 has a second tab 82 formed integral therewith on its lower end on the opposite end from the tab 80. The second tab 82 is disposed within slots 83, which are formed by punching or pushing out a small portion of a common connecting wall 84 of the first body 11. The disposition of the second tab 82 in the slots 83 joins the bodies 11 and 35 to each other at their lower ends with the walls 81 and 84 abutting.

It should be understood that the bodies 11, 35, and 75 are connected at their upper ends to the header 13 through the edges 28 (see FIG. 7) and 29 of the header 13 being disposed in the grooves 30, 36 (see FIG. 5), and 76 (see FIG. 3) in the bodies 11 (see FIG. 1), 35, and 75, respectively. The bodies 11, 35, and 75 are retained in position on the header 13 through the end portion 77 of the body 75 abutting the flange 58 of the manifold plate 50 (see FIG. 2) and the tube 27 (see FIG. 7) being disposed in the inlet 18 of the upper wall 19 of the first body 11 (see FIG. 1). Thus, removal of the tube 27 enables easy replacement of the first body 11 when it is desired to replace the collection chamber 12.

The third body 75 (see FIG. 1) has a pressure regulating chamber 85, which controls the negative pressure applied by the vacuum pump 47 to the collection chamber 12. The pressure regulating chamber 85 includes a first column 86, which has its upper end open to communicate with the atmosphere, and a second column 87, which has a substantially larger cross sectional area than the first column 86. A passage 88 connects the bottom ends of the columns 86 and 87 to each other so that the pressure regulating chamber 85 is substantially U-shaped.

A liquid such as water, for example, is supplied to the passage 88 through a Luer valve 90 in the wall of the pressure regulating chamber 85 and spans the bottoms of the columns 86 and 87. The height of the liquid in the second column 87 controls the negative pressure produced by the vacuum pump 47 in the collection chamber 12. The column 87 has indicia 91 thereon to indicate the level at which the liquid is to be disposed in the second column 87 to have the desired negative pressure produced in the collection chamber 12 by the vacuum pump 47.

The second column 87 has a circular outlet opening 92 (see FIG. 3) in its upper wall 93 in alignment with a circular passage 94 extending through the wall 23 of the header 13. The outlet opening 92 has one of the gaskets 25 disposed therein to form a seal between the opening 92 and the passage 94.

The passage 94 in the wall 23 of the header 13 communicates with the chamber 53. As previously mentioned, the chamber 53 has the vacuum pump 47 (see FIG. 1) connected thereto in addition to having the first column 39 of the liquid seal chamber 38 communicating therewith. Thus, the chamber 53 (see FIG. 3) functions as passage or communicating means.

Accordingly, when the vacuum pump 47 (see FIG. 1) is producing a negative pressure in the collection chamber 12, atmospheric air flows through the liquid spanning the bottom ends of the columns 86 and 87 of the pressure regulating chamber 85 to the chamber 53 (see FIG. 3) to insure that the vacuum pump 47 (see FIG. 1) does not create a negative pressure beyond that selected. Thus, the level of the liquid in the second column 87 controls the selected negative pressure.

The wall 52 (see FIG. 3) of the manifold plate 50 has a circular outlet opening 95 communicating with the atmosphere. The outlet opening 95 is normally closed by a ball check valve 96, which is disposed within a cage 97 having a plurality of openings 97'. The cage 97 is secured to an annular projection 97A on the wall 52 of the manifold plate 50 by any suitable adhesive or bonding means.

Figure 3:
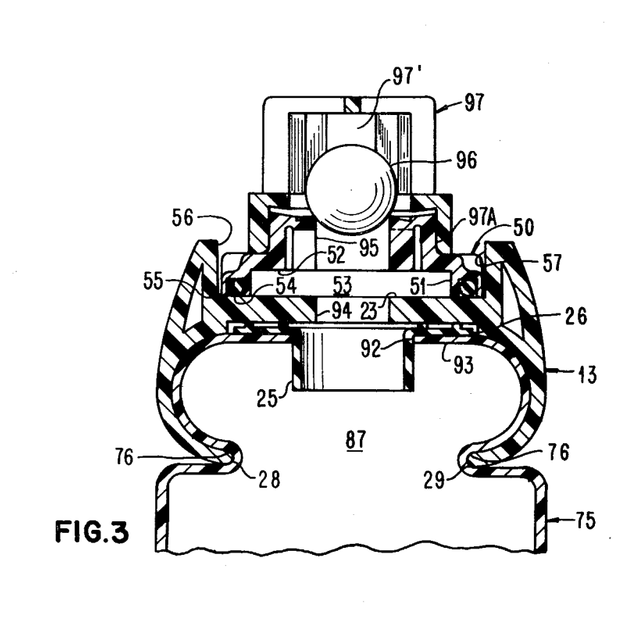
FIG. 3 is a fragmentary sectional view of the modular apparatus of FIG. 1 taken along line 3—3 of FIG. 1 and showing the positive pressure relief valve and the pressure regulating chamber communicating with the same sealed chamber.

Accordingly, if the pressure in the collection chamber 12 (see FIG. 1) increases beyond atmospheric pressure and the pressure necessary to cross the liquid seal chamber 38, this increased pressure is vented through the liquid seal chamber 38 to the chamber 53 (see FIG. 3). This increased positive pressure is then vented to the atmosphere by the ball check valve 96 moving to an open position.

The body 35 (see FIG. 1) has an excess negativity chamber 98 formed therein. The excess negativity chamber 98 is utilized to limit the excess negative pressure in the collection chamber 12 and the pleural cavity of the patient connected to the tube 20 to a predetermined or selected maximum negative pressure greater than the negative pressure produced in the collection chamber 12 by the vacuum pump 47 in conjunction with the pressure regulating chamber 85 in a predetermined period of time. The selected maximum negative pressure is preferably two centimeters of water greater than the pressure selected in the pressure regulating chamber 85 with the predetermined period of time being preferably no more than three minutes.

The excess negativity chamber 98 is a U-shaped tube having a first leg or column 99 with its upper end communicating with the atmosphere through an opening 100 and a second leg or column 101 with its upper end communicating with the reservoir 62. The bottom ends of the legs or columns 99 and 101 are connected by a passage 102. A liquid, such as water, for example, is supplied through the opening 100 to span the bottom ends of the legs or columns 99 and 101.

The leg or column 99 has indicia 103 thereon to indicate the level to which the liquid is to be disposed in the leg or column 99. This level is selected in conjunction with the level of the liquid in the second column 87 of the pressure regulating chamber 85 to determine the selected maximum excess negative pressure. For example, if the second column 87 of the pressure regulating chamber is set at twenty-five centimeters of water, then the column 99 is filled to twenty-seven centimeters of water.

Figure 17:
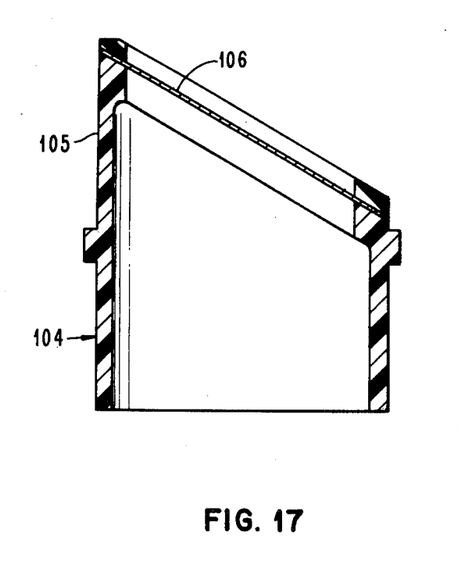
FIG. 17 is a sectional view of a flow control vent means used in controlling the excess negative pressure.
Figure 18:
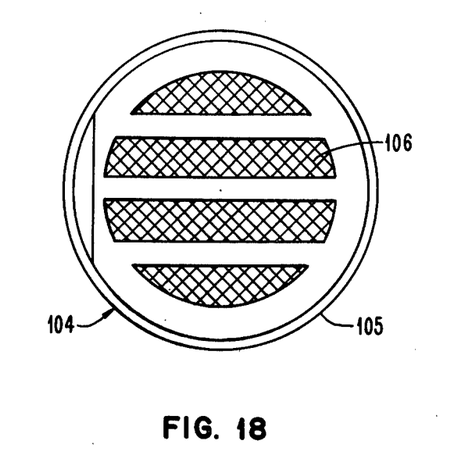
FIG. 18 is a top plan view of the flow control vent means of FIG. 17.

The upper end of the second leg or column 101 communicates with the reservoir 62 through flow control vent means 104 to the reservoir 62. As shown in FIGS. 17 and 18, the flow control vent means 104 includes a body 105, which is formed of a suitable plastic, having a filter 106 supported therein and through which the second leg or column 101 (see FIGS. 1 and 8) of the excess negativity chamber 98 communicates with the reservoir 62.

The material of the filter 106 (see FIGS. 17 and 18) is any suitable material capable of preventing the flow of liquid while allowing the flow of gas therethrough at a desired flow rate so as to function as a liquid check valve. Suitable examples of the material of the filter 106 of the flow control vent means 104 when the liquid is water are sold by Gelman Sciences, Ann Arbor, Mich. under the trademarks Acropor and Versapor.

Accordingly, the flow control vent means 104 prevents the liquid within the excess negativity chamber 98 (see FIG. 1) from flowing to the collection chamber 12 when there is a relatively high negative pressure existing in the pleural cavity of the patient connected to the collection chamber 12 through the tube 20 while still allowing flow of air at a selected flow rate in accordance with the porosity of the material of the filter 106 (see FIGS. 17 and 18) with this flow rate determining the period of time required to limit the excess negative pressure to the selected maximum.

It should be understood that the flow control vent means 104 results in the reduction of excess negativity by air flow through the excess negativity chamber 98 (see FIG. 1) being relatively slow so as not to be able to compensate for the strong gasp of a patient to avoid the possible loss of the liquids from the liquid seal chamber 38. Accordingly, the rate and mechanism of a patient's gasp is such that the excess negativity chamber 98 and the flow control vent means 104 could not always function in time to prevent the loss of liquid from the liquid seal chamber 38 without the bypass tube 62A (see FIG. 8).

Considering the operation of the drainage apparatus 10 (see FIG. 1) with the tube 20 connected to the pleural cavity of the patient and the vacuum pump 47 connected to the liquid seal chamber 38, the vacuum pump 47 produces a desired negative pressure in the collection chamber 12 in accordance with the height of the liquid in the second column 87 of the pressure regulating chamber 85. For example, the negative pressure could be twenty-five centimeters of water.

If the negative pressure in the pleural cavity of the patient increases beyond that produced by the vacuum pump 47 in conjunction with the pressure regulating chamber 85, any increase in this negative pressure beyond the predetermined or selected maximum, as determined by the level of the liquid in the first leg or column 99 of the excess negativity chamber 98, results in atmospheric air flowing from the opening 100 through the liquid in the excess negativity chamber 98 into the collection chamber 12. Thus, the increase in the negative pressure in the pleural cavity of the patient connected to the tube 20 is limited. The flow rate of the air is controlled by the porosity of the material of the filter 106 (see FIGS. 17 and 18) of the flow control vent means 104.

It should be understood that limiting the excess negative pressure in the pleural cavity is the invention of Edward P. Todd and is shown, described, and claimed in the copending patent application of Edward P. Todd for "Drainage Apparatus Having Excess Negativity Pressure Control," Ser. No. 386,241, filed June 8, 1982. Furthermore, the structures of the bypass tube 62A (see FIG. 8), the excess negativity chamber 98 (see FIG. 1), and the flow control valve means 104 are the invention of Edward P. Todd and Eugene E. Weilbacher and are shown, described, and claimed in the copending patent application of Edward P. Todd et al for "Modular Drainage Apparatus Having Excess Negativity Control," Ser. No. 386,252, filed June 8, 1982.

While the modular apparatus of the present invention has been shown and described with respect to utilization with the invention of Edward F. Todd as described in the aforesaid Todd application and the invention of Edward P. Todd and Eugene E. Weilbacher as described in the aforesaid Todd et al application, it should be understood that the modular apparatus of the present invention may be readily utilized anywhere that it is desired to support a plurality of bodies with a common or single support means having fluid communication means between chambers in various bodies. Thus, the modular apparatus of the present invention is not limited to a drainage apparatus for a pleural cavity.

An advantage of this invention is that it is lightweight. Another advantage of this invention is that it is easy to assemble. A further advantage of this invention is that the collection chamber may be easily replaced when necessary.

For purposes of exemplification, a particular embodiment of the invention has been shown and described according to the best present understanding thereof. However, it will be apparent that changes and modifications in the arrangement and construction of the parts thereof may be resorted to without departing from the spirit and scope of the invention.

I claim:

1. A modular apparatus including:
    a plurality of bodies;
    each of said bodies including at least one chamber having an upper wall and a pair of side walls;
    said upper wall of said one chamber of each of said bodies having at lesat one opening therein;
    each of said bodies having a separate groove in each of said pair of side walls adjacent at least said upper wall of said one chamber;
    support means for suspended support of each of said bodies and for longitudinal movement of each of said bodies on said support means;
    said support means having a longitudinally extending wall;
    said support means having means for disposition within said grooves in each of said bodies for support of each of said bodies and for longitudinal movement of each of said bodies on said support means;
    said support means having at least one passage means;
    and said longitudinally extending wall of said support means having openings therein to enable at least said one opening in said upper wall of said one chamber of each of said bodies to communicate with one of said passage means of said support means so that said one chamber of one of said bodies communicates with said one chamber of another of said bodies when said bodies are positioned on said support means so as to provide communication between said one chamber of each of at least two of said bodies.

2. The modular apparatus according to claim 1 including body position control means on at least one of said support means and said bodies to control the position of each of said bodies on said support means to insure that each of said bodies has said opening in said upper wall of said one chamber communicating with one of said openings in said longitudinally extending wall of said support means.

3. The modular apparatus according to claim 2 including:
   said bodies are slidably supported by said support means for longitudinal movement;
   and said body position control means retaining said bodies on said support means at selected longitudinal positions on said support means.

4. The modular apparatus according to claim 1 including:
   said support means having two passage means;
   said support means supporting three of said bodies;
   a first of said bodies having said one chamber communicating with one of said passage means through said one opening in said upper wall of said one chamber;
   a second of said bodies having two openings in said upper wall of said one chamber, said one chamber communicating with said one passage means through one of said openings to communicate with said one chamber of said first body and said one chamber communicating with the other of said passage means remote from its communication with said one passage means through the other of said openings;
   and a third of said bodies having said one chamber communicating with said other passage means through said one opening in said upper wall of said one chamber to communicate with said one chamber of said second body.

5. The modular apparatus according to claim 1 in which said one opening in said upper wall of said one chamber of each of said bodies has gasket means therein to prevent fluid leakage between said one chamber having said opening with said gasket means therein and said passage means communicating with said one chamber having said opening with said gasket means therein.

6. A modular apparatus including:
   three bodies;
   each of said bodies including at least one chamber having an upper wall;
   said upper wall of said one chamber of each of said bodies having at least one opening therein;
   each of said bodies having a groove on each side thereof adjacent at least said upper wall of said one chamber;
   support means to support each of said bodies;
   said support means having a longitudinally extending wall;
   said support means having means for disposition within said grooves in each of said bodies to support each of said bodies to have said upper wall of at least said one chamber abut said longitudinally extending wall of said support means;
   said support means having two passage means;
   said longitudinally extending wall of said support means having openings therein to enable at least said one opening in said upper wall of said one chamber of each of said bodies to communicate with one of said passage means of said support means so that said one chamber of one of said bodies communicates with said one chamber of another of said bodies;
   a first of said bodies having said one chamber communicating with one of said passage means through said one opening in said upper wall of said one chamber;
   a second of said bodies having two openings in said upper wall of said one chamber, said one chamber communicating with said one passage means through one of said openings to communicate with said one chamber of said first body and said one chamber communicating with the other of said passage means remote from its communication with said one passage means through the other of said openings;
   and a third of said bodies having said one chamber communicating with said other passage means through said one opening in said upper wall of said one chamber to communicate with said one chamber of said second body.

7. The modular apparatus according to claim 6 in which:
   said one chamber of said third body is a collection chamber having inlet means for connection to a pleural cavity of a body to receive fluids therefrom;
   said collection chamber communicating with said other passage means;
   said one chamber of said second body includes a liquid seal chamber;
   said one passage means includes means to enable a negative pressure to be applied to said liquid seal chamber and said collection chamber and to remove gases from the fluids in said collection chamber to said liquid seal chamber;
   and said one chamber of said first body is a U-shaped regulating chamber having one end exposed to the atmosphere and its other end connected to said one passage means, said U-shaped regulating chamber adapted to have a selected quantity of liquid therein to control the negative pressure produced in said liquid seal chamber and said collection chamber.

8. The modular apparatus according to claim 7 in which:
   said inlet means includes an opening in said upper wall of said one chamber of said third body and an opening in said longitudinally extending wall of said support means;
   and means supported by said support means for disposition in said openings of said inlet means to position said third body on said support means at a selected position and retain said third body at its selected position.

9. The modular apparatus according to claim 6 in which said one opening in said upper wall of said one chamber of each of said first and third bodies and each of said two openings in said upper wall of said one chamber of said second body has gasket means therein to form a seal with said communicating opening in said longitudinally extending wall of said support means.

10. A modular apparatus including:

a plurality of bodies;
each of said bodies including at least one chamber having an upper wall;
said upper wall of said one chamber of each of said bodies having at least one opening therein;
each of said bodies having a groove on each side thereof adjacent at least said upper wall of said one chamber;
support means to support each of said bodies;
said support means having a longitudinally extending wall;
said support means having means for disposition within said grooves in each of said bodies to support each of said bodies to have said upper wall of at least said one chamber abut said longitudinally extending wall of said support means;
said support means having at least one passage means;
said longitudinally extending wall of said support means having openings therein to enable at least said one opening in said upper wall of said one chamber of each of said bodies to communicate with one of said passage means of said support means so that said one chamber of one of said bodies communicates with said one chamber of another of said bodies;
and said one opening in said upper wall of said one chamber of each of said bodies having gasket means therein to form a seal with said communicating opening in said longitudinally extending wall of said support means.

11. A modular apparatus including:
a plurality of bodies;
each of said bodies including at least one chamber having an upper wall;
said upper wall of said one chamber of each of said bodies having at least one opening therein;
each of said bodies having a groove on each side thereof adjacent at least said upper wall of said one chamber;
support means to support each of said bodies;
said support means having a longitudinally extending wall;
said support means having means for disposition within said grooves in each of said bodies to support each of said bodies to have said upper wall of at least said one chamber abut said longitudinally extending wall of said support means;
said support means having at least one passage means;
said longitudinally extending wall of said support means having openings therein to enable at least said one opening in said upper wall of said one chamber of each of said bodies to communicate with one of said passage means of said support means so that said one chamber of one of said bodies communicates with said one chamber of another of said bodies;
body position control means on at least one of said support means and said bodies to control the position of each of said bodies on said support means to insure that each of said bodies has said opening in said upper wall of said one chamber communicating with one of said openings in said longitudinally extending wall of said support means;
said bodies being slidably supported by said support means;
said body position control means retaining said bodies on said support means at selected positions on said support means;
said body position control means including at least first and second means separate from each other and supported by said support means;
said first means cooperating only with one of said bodies at one end of said bodies to limit its longitudinal movement along said support means;
and said second means cooperating only with another of said bodies at the other end of said bodies to limit longitudinal movement of said another body along said support means.

12. A modular apparatus including:
a plurality of bodies;
each of said bodies including at least one chamber having an upper wall;
each of said bodies having a separate longitudinal groove on opposite sides thereof adjacent at least said upper wall of said one chamber but spaced from said upper wall of said one chamber;
support means to support each of said bodies;
said support means having first and second longitudinally extending means on opposite sides of each of said bodies, one of said first and second longitudinally extending means being disposed within said longitudinal groove in each of said bodies on one side thereof and the other of said first and second longitudinally extending means being disposed within said longitudinal groove in each of said bodies on the other side thereof;
said upper wall of said one chamber of each of said bodies having at least one opening therein;
at least one passage means;
and at least said one opening in said upper wall of said one chamber of each of said bodies communicating with one of said passage means so that said one chamber of one of said bodies communicates with said one chamber of another of said bodies.

13. The modular apparatus according to claim 12 including:
said support means having two passage means;
said support means supporting three of said bodies;
a first of said bodies having said one chamber communicating with one of said passage means through said one opening in said upper wall of said one chamber;
a second of said bodies having two openings in said upper well of said one chamber, said one chamber communicating with said one passage means through one of said openings to communicate with said one chamber of said first body and said one chamber communicating with the other of said passage means remote from its communication with said one passage means through the other of said openings;
and a third of said bodies having said one chamber communicating with said other passage means through said one opening in said upper wall of said one chamber to communicate with said one chamber of said second body.

14. The modular apparatus according to claim 13 in which:
said one chamber of said third body is a collection chamber having inlet means for connection to a pleural cavity of a body to receive fluids therefrom;
said collection chamber communicating with said other passage means;
said one chamber of said second body includes a liquid seal chamber;

said one passage means includes means to enable a negative pressure to be applied to said liquid seal chamber and said collection chamber and to remove gases from the fluids in said collection chamber to said liquid seal chamber;

and said one chamber of said first body is a U-shaped regulating chamber having one and exposed to the atmosphere and its other end connected to said one passage means, said U-shaped regulating chamber adapted to have a selected quantity of liquid therein to control the negative pressure produced in said liquid seal chamber and said collection chamber.

15. The modular apparatus according to claim 14 including:

said bodies are slidably supported by said support means;

first body position means supported by said support means cooperating only with one of said bodies at one end of said bodies to limit its movement along said support means;

and second body position means supported by said support means cooperating only with another of said bodies at the other end of said bodies to limit movement of said another body along said support means.

16. The modular apparatus according to claim 14 in which:

said first longitudinally extending means and said second longitudinally extending means slidably support each of said bodies;

and means controls the position of each of said bodies on said support means.

17. The modular apparatus according to claim 12 in which:

said first longitudinally extending means and said second longitudinally extending means slidably support each of said bodies;

and means controls the position of each of said bodies on said support means.

18. The modular apparatus according to claim 12 in which:

said support means has a longitudinally extending wall;

and said first longitudinally extending means extends from one side of said longitudinally extending wall and said second longitudianlly extending means extends from the opposite side of said longitudinally extending wall.

19. A modular apparatus including:

a plurality of bodies;

each of said bodies including at least one chamber having an upper wall;

longitudinally extending support means to slidably support each of said bodies on said longitudinally extending support means for longudinal movement on said longitudinally extending support means;

means on each of said bodies for cooperating support with said longitudianally extending support means to enable longitudinal movement of each of said bodies on said longitudinally extending support means;

body position control means on at least one of said longitudinally extending support means and said bodies to position each of said bodies at a selected longitudinal position on said longitudinally extending support means and to retain each of said bodies at the selected longitudinal position on said longitudinally extending support means;

said upper wall of said one chamber of each of said bodies having at least one opening therein;

at least one passage means;

and at least said one opening in said upper wall of said one chamber of each of said bodies communicating with one of said passage means so that said one chamber of one of said bodies communicates with said one chamber of another of said bodies when said bodies are supported on said longitudinally extending support means at the selected longitudinal positions.

20. The modular apparatus according to claim 19 including:

two passage means;

said longitudinally extending support means supporting three of said bodies;

a first of said bodies having said one chamber communicating with one of said passage means through said one opening in said upper wall of said one chamber;

a second of said bodies having two openings in said upper wall of said one chamber, said one chamber communicating with said one passage means through one of said openings to communicate with said one chamber of said first body and said one chamber communicating with the other of said passage means remote from its communication with said one passage means through the other of said openings;

and a third of said bodies having said one chamber communicating with said other passage means through said one opening in said upper wall of said one chamber to communicate with said one chamber of said second body.

21. A modular apparatus including:

three bodies;

each of said bodies including at least one chamber having an upper wall;

support means to slidably support each of said bodies on said support means;

body position control means supported by said support means to position each of said bodies at a selected position on said support means and to retain each of said bodies at the selected position on said support means;

said upper wall of said one chamber of each of said bodies having at least one opening therein;

said support means having two passage means;

a first of said bodies having said one chamber communicating with one of said passage means through said one opening in said upper wall of said one chamber;

a second of said bodies having two openings in said upper wall of said one chamber, said one chamber cummunicating with said one passage means through one of said openings to communicate with said one chamber of said first body and said one chamber communicating with the other of said passage means remote from its communication with said one passage means through the other of said openings;

and a third of said bodies having said one chamber communicating with said other passage means through said one opening in said upper wall of said one chamber to communicate with said one chamber of said second body.

22. The modular apparatus according to claim 21 in which:

said one chamber of said third body is a collection chamber having inlet means for connection to a pleural cavity of a body to receive fluids therefrom;

said collection chamber communicating with said other passage means;

said one chamber of said second body includes a liquid seal chamber;

said one passage means includes means to enable a negative pressure to be applied to said liquid seal chamber and said collection chamber and to remove gases from the fluids in said collection chamber to said liquid seal chamber;

and said one chamber of said first body is a U-shaped regulating chamber having one end exposed to the atmosphere and its other end connected to said one passage means, said U-shaped regulating chamber adapted to have a selected quantity of liquid therein to control the negative pressure produced in said liquid seal chamber and said collection chamber.

23. A modular apparatus including:

a plurality of bodies;

each of said bodies including at least one chamber having an upper wall and a pair of side walls;

said upper wall of said one chamber of each of said bodies having at least one opening therein;

each of said bodies having a groove in each of said pair of side walls adjacent at least said upper wall of said one chamber;

support means to support each of said bodies for longitudinal movement on said support means;

said support means haivng means for disposition within said grooves in each of said bodies for support of each of said bodies and for longitudinal movement of each of said bodies on said support means;

at least one passage means;

at least said one opening in said upper wall of said one chamber of each of said bodies communicating with one of said passage means so that said one chamber of one of said bodies communicates with said one chamber of another of said bodies when said bodies are positioned on said support emans so as to provide communication between said one chamber of each of at least two of said bodies;

body position control means on at least one of said support means and said bodies to control the longitudinal position of each of said bodies on said support means;

said body position control means including at least first and second means separate from each other;

said first means cooperating only with one of said bodies at one end of said bodies to limit its longitudinal movement along said support means;

and said second means cooperating only with another of said bodies at the other end of said bodies to limit longitudinal movement of said another body along said support means.

* * * * *

UNITED STATES PATENT AND TRADEMARK OFFICE
CERTIFICATE OF CORRECTION

PATENT NO. : 4,465,483
DATED : August 14, 1984
INVENTOR(S) : Eugene E. Weilbacher It is certified that error appears in the above—identified patent and that said Letters Patent is hereby corrected as shown below:

ON THE TITLE PAGE IN THE TITLE

"MODULAR DRAINAGE APPARATUS" should read --- MODULAR APPARATUS INCLUDING SUPPORTED BODIES ---.

Column 1, line 2, "MODULAR DRAINAGE APPARATUS" should read --- MODULAR APPARATUS INCLUDING SUPPORTED BODIES ---.

Column 14, line 47, "well" should read --- wall ---.

Column 15, line 7, "and" should read --- end ---.

Column 18, line 17, "emans" should read --- means ---.

Signed and Sealed this

Twelfth Day of March 1985

[SEAL]

Attest:

DONALD J. QUIGG

Attesting Officer  Acting Commissioner of Patents and Trademarks